(12) United States Patent
Nishikawa

(10) Patent No.: US 8,173,157 B2
(45) Date of Patent: May 8, 2012

(54) PHARMACEUTICAL COMPOSITION COMPRISING PHENYLAMIDINE DERIVATIVE AND METHOD OF USING THE PHARMACEUTICAL COMPOSITION IN COMBINATION WITH ANTIFUNGAL AGENT

(75) Inventor: Hiroshi Nishikawa, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 342 days.

(21) Appl. No.: 12/443,750

(22) PCT Filed: Oct. 3, 2007

(86) PCT No.: PCT/JP2007/069341
§ 371 (c)(1),
(2), (4) Date: Mar. 31, 2009

(87) PCT Pub. No.: WO2008/044562
PCT Pub. Date: Apr. 17, 2008

(65) Prior Publication Data
US 2010/0098750 A1     Apr. 22, 2010

(30) Foreign Application Priority Data
Oct. 6, 2006 (JP) .................................. 2006-274709

(51) Int. Cl.
| A61K 9/127 | (2006.01) |
| A61M 36/14 | (2006.01) |
| A01N 25/00 | (2006.01) |
| A01N 43/00 | (2006.01) |
| A61K 31/74 | (2006.01) |
| A61K 9/48 | (2006.01) |
| A61K 9/64 | (2006.01) |
| A61K 9/20 | (2006.01) |
| A61K 31/435 | (2006.01) |
| A61K 31/445 | (2006.01) |
| C07D 401/00 | (2006.01) |
| C07D 211/00 | (2006.01) |
| C07C 229/00 | (2006.01) |

(52) U.S. Cl. .................. 424/450; 424/1.65; 424/78.07; 424/405; 424/451; 424/452; 424/456; 424/464; 424/465; 514/183; 514/252.1; 514/277; 514/315; 514/317; 514/331; 546/184; 546/192; 546/229; 546/231; 546/233; 560/168

(58) Field of Classification Search .................. 424/450, 424/1.65, 78.07, 405, 451, 452, 456, 464, 424/465; 514/183, 252.1, 277, 315, 317, 514/331; 546/184, 192, 229, 231, 233; 560/168
See application file for complete search history.

(56) References Cited

U.S. PATENT DOCUMENTS
| 4,782,059 A * | 11/1988 | Gadebusch et al. ...... 514/254.07 |
| 6,875,740 B1 * | 4/2005 | Ikeda et al. .................... 514/3.6 |
| 7,291,617 B2 | 11/2007 | Hayashi et al. |
| 2005/0124536 A1 | 6/2005 | Ikeda et al. |
| 2008/0319016 A1 | 12/2008 | Hayashi et al. |
| 2009/0087480 A1 | 4/2009 | Nomura et al. |
| 2010/0016602 A1 * | 1/2010 | Hayashi ........................ 546/247 |

FOREIGN PATENT DOCUMENTS
| CN | 1596897 A | 3/2005 |
| EP | 1 481 966 A1 | 12/2004 |
| EP | 1 767 526 A1 | 3/2007 |
| EP | 1 967 190 A1 | 9/2008 |
| JP | 11 504931 | 5/1999 |
| JP | 3288051 | 3/2002 |
| JP | 2003 527314 | 9/2003 |
| JP | 2005-97298 | 4/2005 |
| WO | WO96/35423 A2 * | 11/1996 |
| WO | WO9810782 A2 * | 3/1998 |
| WO | WO 2005/026323 A2 | 3/2005 |

(Continued)

OTHER PUBLICATIONS

M.D. Johnson et al., "Combination Antifungal Therapies," Mar. 2004, Antimicrobial Agents & Chemotherapy, vol. 48, No. 3, pp. 693-715.*
U.S. Appl. No. 12/159,527, filed Jun. 27, 2008, Hayashi.
Junichi Mitsuyama, et al., "In Vitro and In Vivo Antifungal Activities of T-2307, a Novel Arylamidine", Antimicrobial Agents and Chemotherapy, vol. 52, No. 4, XP-002557660, Apr. 2008, pp. 1318-1324.

(Continued)

*Primary Examiner* — Johann Richter
*Assistant Examiner* — Jane C Osewcki
(74) *Attorney, Agent, or Firm* — Oblon, Spivak, McClelland, Maier & Neustadt, L.L.P.

(57) ABSTRACT

A pharmaceutical composition comprising a phenylamidine derivative or a salt thereof, represented by a general formula,

[CHEMICAL FORMULA 1]

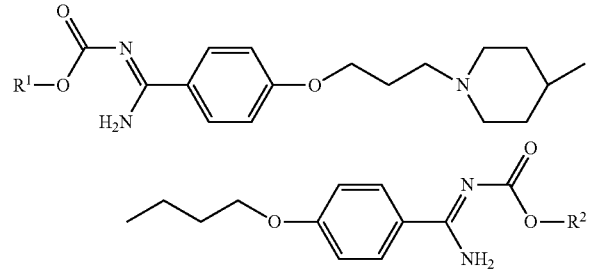

wherein $R^1$ and $R^2$ may be same or different, and represent an optionally substituted $C_{3-4}$alkyl group; and one or more agents selected from azole antifungal agents, polyene antifungal agents, candin antifungal agents and fluoropyrimidine antifungal agents, and a method for combination use of the phenylamidine derivative or a salt thereof and the agents are useful for treating fungal infections caused by a fungal pathogen.

20 Claims, No Drawings

FOREIGN PATENT DOCUMENTS

| | | |
|---|---|---|
| WO | 2006 003881 | 1/2006 |
| WO | WO 2006/011499 A1 | 2/2006 |
| WO | 2006 109642 | 10/2006 |
| WO | WO2006109642 A1 * | 10/2006 |
| WO | WO2006/003881 A2 * | 12/2006 |
| WO | WO 2007/055197 A1 | 5/2007 |
| WO | 2007 074868 | 7/2007 |

OTHER PUBLICATIONS

M. H. Beers, et al., "The Merck Manual",158/ Systemic Fungal Diseases, XP-002557124, 1999, pp. 1209-1213.

* cited by examiner

PHARMACEUTICAL COMPOSITION COMPRISING PHENYLAMIDINE DERIVATIVE AND METHOD OF USING THE PHARMACEUTICAL COMPOSITION IN COMBINATION WITH ANTIFUNGAL AGENT

CROSS-REFERENCE TO RELATED APPLICATIONS

This application is a 371 of PCT/JP07/69341 filed Oct. 3, 2007 and claims the benefit of JP 2006-274709 filed Oct. 6, 2006.

FIELD OF THE INVENTION

The present invention relates to a pharmaceutical composition which is useful for the treatment of fungal infections caused by fungal pathogens and which comprises a new phenylamidine derivative or a salt thereof, and one or more agents selected from azole antifungal agents, polyene antifungal agents, candin antifungal agents and fluoropyrimidine antifungal agents. The present invention also relates to a method of using the new phenylamidine derivative or a salt in combination with the agents for treating fungal infections.

BACKGROUND ART

Serious deep mycosis such as invasive candidiasis can often be a fatal disease. In the past, it has been considered that the principal protective mechanism on the side of a host organism against fungi such as *Candida* is nonspecific immunization by neutrophils. When this protective mechanism functions normally there is little risk of becoming infected with fungi. However, in recent years, the risk of suffering from deep mycosis has been boosted because of the increased number of patients with underlying diseases decreasing the immunological function of the body, such as malignant tumors (in particular, hemopoietic malignant tumors such as acute leukemia or malignant lymphoma) and AIDS, frequent use of anticancer agents or immunosuppressants, heavy use of antibacterial antibiotics or steroid hormones, long-term use of central venous hyperalimentation or venous catheterization and the like (Non-Patent Document 1).

Agents used for the treatment of such deep mycosis are very few, when compared to antibacterial agents used, and include only amphotericin B, flucytosine, miconazole, fluconazole, fosfluconazole, itraconazole, voriconazole, micafungin and the like.

On the other hand, there is an increasing need for safe and effective agents against opportunistic fungal infections caused by fungal pathogens such as *Candida, Cryptococcus* and *Aspergillus*.

While the agents that are used at present, for example, amphotericin B, have an extremely strong fungicidal action, they have a problem regarding side effects such as nephrotoxicity, so that their clinical usage is limited. Flucytosine has problems with the development of resistance. Micafungin has a low activity against the *Cryptococcus*. Azoles such as fluconazole and voriconazole are most frequently used at present due to their balance between effectiveness and safety, although their fungicidal action is inferior to that of amphotericin B (Non-Patent Documents 2 and 3).

Methods for combination use of antifungal agents are being used for purposes such as to boost treatment effects (Non-Patent Document 4). Research is also progressing into the combination of antifungal agents (Patent Documents 1, 2 and 3). However, the number of agents being combined is limited, meaning that satisfactory treatment effects cannot be guaranteed.

Further, phenylamidine derivatives having antifungal activity are known (Patent Document 4).

Patent Document 1: Japanese Patent No. 3288051
Patent Document 2: JP-A-11-504931
Patent Document 3: JP-A-2003-527314
Patent Document 4: International Patent Publication No. WO2006/003881
Non-Patent Document 1: Rinsho to Biseibutsu (Clinics and Microorganisms), Vol. 17, pp. 265-266, 1990
Non-Patent Document 2: Rinsho to Biseibutsu (Clinics and Microorganisms), Vol. 21, pp. 277-283, 1994
Non-Patent Document 3: Rinsho to Biseibutsu (Clinics and Microorganisms), Vol. 30, pp. 595-614, 2003
Non-Patent Document 4: Diagnosis and treatment guideline of deep mycosis, PP. 20, 29, Ishiyaku Publishers, Inc., 2003

DISCLOSURE OF THE INVENTION

Problem to be Solved by the Invention

Desirable are a pharmaceutical composition which is useful for treating fungal infections and which has strong antifungal activity yet few side effects, and a method for combination use of antifungal agents.

Means to Solve the Problem

Under such circumstances, as a result of intensive study, the present inventors discovered that a pharmaceutical composition comprising a phenylamidine derivative or a salt thereof, represented by the general formula [1] which is a new compound:

[Chemical Formula 1]

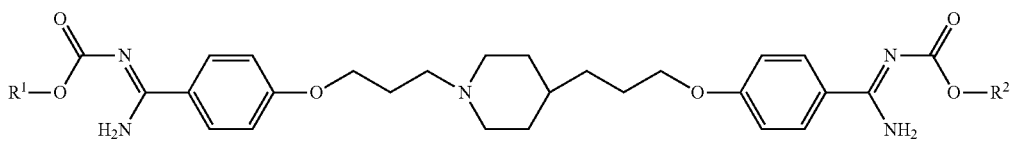

wherein $R^1$ and $R^2$ may be same or different, and represent an optionally substituted $C_{3-4}$alkyl group; and one or more agents selected from azole antifungal agents, polyene antifungal agents, candin antifungal agents and fluoropyrimidine antifungal agents, has a strong antifungal activity and is useful for treating fungal infections, and that a method for combination use of these antifungal agents is useful for treating fungal infections, thereby arriving at the present invention.

EFFECT OF THE INVENTION

The pharmaceutical composition comprising the new phenylamidine derivative or a salt thereof, and one or more agents selected from azole antifungal agents, polyene antifungal agents, candin antifungal agents and fluoropyrimidine antifungal agents, has strong antifungal activity and is useful for treating fungal infections. The method for combination use of these antifungal agents is useful as an excellent treatment method of fungal infections.

BEST MODE FOR CARRYING OUT THE INVENTION

The present invention will now be described in more detail.

In the present specification, unless otherwise noted, a halogen atom refers to a fluorine atom, a chlorine atom, a bromine atom, or an iodine atom; and a $C_{3-4}$alkyl group means propyl, isopropyl, n-butyl, sec-butyl, isobutyl and tert-butyl.

Examples of the salts of the compound represented by general formula [1] include the salts of mineral acids, such as hydrochloric acid, hydrobromic acid, phosphoric acid and sulfuric acid; the salts of organic carboxylic acids, such as succinic acid, maleic acid and fumaric acid; the salts of sulfonic acids such as methanesulfonic acid, benzenesulfonic acid, p-toluenesulfonic acid, mesitylenesulfonic acid and naphthalenesulfonic acid.

Preferred salts of the compound represented by the general formula [1] include pharmacologically acceptable salts.

For the substituent of unsubstituted or substituted $C_{3-4}$alkyl group in $R^1$ and $R^2$, halogen atom, hydroxyl group and carboxyl group are given.

In compounds of the general formula [1] used for the present invention, the preferred compounds are the compounds given below.

Compounds in which $R^1$ is a $C_{3-4}$alkyl group are preferred, compounds in which $R^1$ is a propyl, isopropyl or n-butyl group are more preferred, and compounds in which $R^1$ is n-butyl group are furthermore preferred.

Compounds in which $R^2$ is a $C_{3-4}$alkyl group are preferred, compounds in which $R^2$ is a propyl, isopropyl or n-butyl group are more preferred, and compounds in which $R^2$ is n-butyl group are furthermore preferred.

Compounds in which $R^1$ and $R^2$ are a same group are preferred.

Concretely, for the compound of the general formula [1], the following compound is preferred.

[Chemical Formula 2]

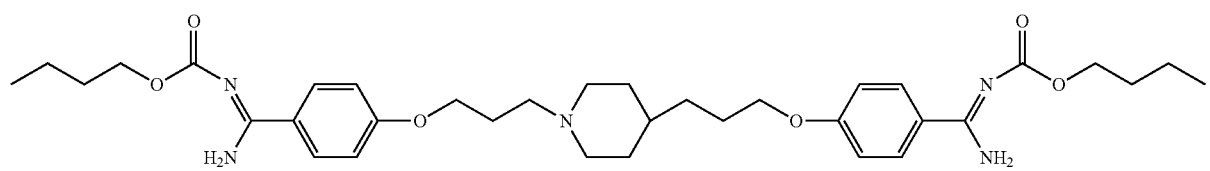

Next, manufacturing methods of present invention compounds are explained.

The compounds of the present invention are produced by the combination of conventional methods per se, for example, can be manufactured by the methods shown in next.

[Manufacturing Method]

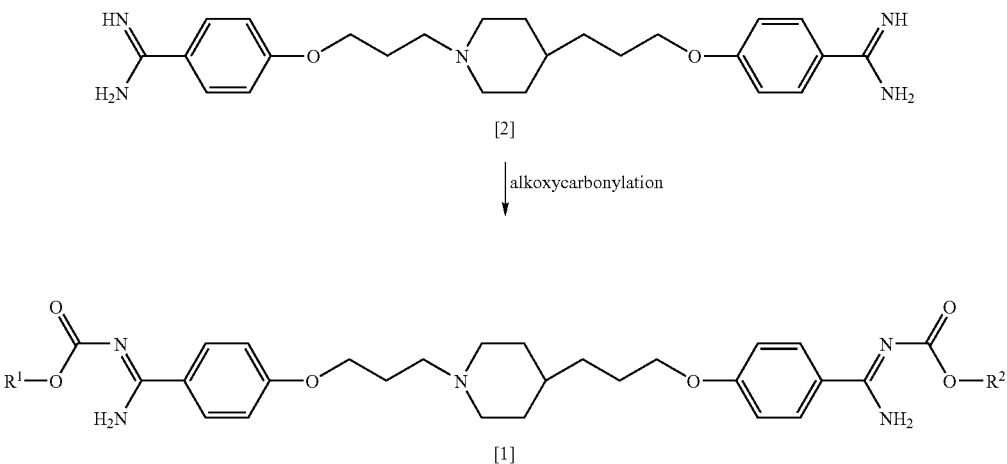

wherein $R^1$ and $R^2$ have the same meanings as the above.

The compound of the general formula [1] can be manufactured by subjecting the compound of formula [2] and the reactive derivative to alkoxycarbonylation reaction in the presence or absence of base.

For a solvent used in this reaction, it is not limited particularly as long as it does not affect the reaction adversely, for example, amides such as N,N-dimethylformamide, N,N-dimethylacetamide and 1-methyl-2-pyrolidone; halogenated hydrocarbons such as dichloromethane, chloroform and dichloroethane; aromatic hydrocarbons such as benzene, toluene and xylene; ethers such as dioxane, tetrahydrofuran, anisole, di(ethylene glycol) dimethyl ether, di(ethylene glycol) diethyl ether and ethylene glycol monomethyl ether; nitriles such as acetonitrile; sulfoxides such as dimethyl sulfoxide; ketones such as acetone and 2-butanone; esters such as ethyl acetate; carboxylic acids such as acetic acid; heteroaromatics such as pyridine and water are given, and these may be mixed and the mixture may be used.

For a reactive derivative used in this reaction, for example, chlorocarbonic esters such as propyl chloroformate, isopropyl chloroformate, butyl chloroformate and isobutyl chloroformate; active esters such as 4-nitrophenyl propylcarbonate, 4-nitrophenyl isopropylcarbonate, butyl 4-nitrophenylcarbonate and isobutyl 4-nitrophenylcarbonate are given. These reactive derivatives may be used after preparation in situ without isolating.

For a base used in this reaction by a wish, for example, metal alkoxides such as sodium methoxide, sodium ethoxide, potassium tert-butoxide and sodium tert-butoxide; inorganic bases such as sodium hydroxide, potassium hydroxide, sodium hydrogen carbonate, sodium carbonate, potassium carbonate, sodium hydride and potassium hydride and organic bases such as triethylamine, N,N-diisopropylethylamine, 1,8-diazabicyclo[5.4.0]undec-7-ene(DBU) and pyridine are given.

The amount of the reactive derivative and the base used are 2-100 times mole per that of the compound of the formula [2], and are preferably 2-10 times mole.

This reaction may be carried out at −20 to 100° C., preferably at 0 to 50° C. for 1 minute to 24 hours.

For a compound in the manufacturing process described above, solvates, hydrates and various kinds of crystals can be used.

The compound of the formula [2] which is a raw material of production of the present invention is manufactured by the combination of conventional methods per se, for example, it can be manufactured by the methods as described in patent document 4.

Examples of the azole antifungal agents used in the present invention include triazole antifungal agents, such as fluconazole, fosfluconazole, itraconazole, voriconazole, posaconazole, ravuconazole, BMS-379224, BAL-8557 and CS-758, as well as imidazole antifungal agents, such as ketoconazole, miconazole, bifonazole, lanoconazole and luliconazole.

Preferred examples of the azole antifungal agents include triazole antifungal agents, such as fluconazole, fosfluconazole, itraconazole, voriconazole, posaconazole, ravuconazole, BMS-379224, BAL-8557 and CS-758. More preferred are fluconazole, fosfluconazole, voriconazole and itraconazole, and even more preferred are fluconazole and voriconazole.

Examples of the polyene antifungal agents used in the present invention include, for example, amphotericin B and liposomal formulations thereof (e.g., Abelcet (trade name) or AmBisome (trade name)), nystatin, trichomycin, SPK-843 and pimaricin.

Preferred examples of the polyene antifungal agents include amphotericin B and liposomal formulations thereof.

Examples of the candin antifungal agents used in the present invention include, for example, micafungin, caspofungin, anidulafungin and aminocandin.

Preferred examples of the candin antifungal agents used include micafungin.

Examples of the fluoropyrimidine antifungal agents used in the present invention include, for example, flucytosine.

The administration route of the phenylamidine derivative or the salt thereof represented by the general formula [1] is not especially limited, and the phenylamidine derivative or the salt thereof can be administered intravenously, orally, intramuscularly, subcutaneously or by some other administration route. Further, the phenylamidine derivative or the salt thereof represented by the general formula [1] can also be administered simultaneously, separately, or in a specific order, with the azole antifungal agents, polyene antifungal agents, candin antifungal agents and fluoropyrimidine antifungal agents.

The pharmaceutical composition of the present invention exhibits excellent action against fungi such as *Candida*, *Cryptococcus* and *Aspergillus*. The pharmaceutical composition of the present invention exhibits especially excellent action against *Candida* such as *Candida albicans*, *Candida glabrata*, *Candida guilliermondii*, *Candida kefyr*, *Candida krusei*, *Candida parapsilosis*, *Candida stellatoidea*, *Candida tropicalis* and *Candida lusitaniae*; *Cryptococcus* such as *Cryptococcus neoformans*; *Aspergillus* such as *Aspergillus clavatus*, *Aspergillus flavus*, *Aspergillus fumigatus*, *Aspergillus nidulans*, *Aspergillus niger*, *Aspergillus terreus*, *Aspergillus versicolor* and *Aspergillus restrictus*.

The pharmaceutical composition of the present invention is effective in the prevention and treatment of a variety of fungal infections, such as candidosis, cryptococcosis and aspergillosis.

With the pharmaceutical composition of the present invention, more serious fungal infections can be treated. In addition, since a strong antifungal action is exhibited even if the amount of each of the agents that are administered is lowered, the side effects of the respective agents can be reduced.

When pharmaceutical compositions of the present invention are used, pharmaceutical aids such as excipients, carrier and diluting agents, those of which are used by pharmaceutical preparations, may be usually mixed appropriately, and these can be administered to conventional methods in oral or parenteral in morphology such as tablets, encapsulated formulations, powders, syrups, granules, pills, suspending agents, emulsions, liquid drugs, powder formulations, suppositories, ophthalmic washes, nose drops, ear drops, patches, ointments or injections. In addition, medication methods, dosages and the number of medication can be selected appropriately according to an age, body weight and symptom of a patient. Usually, for an adult, dosage of 0.01 to 1000 mg/kg may be divided into several portions and administered once a day from one to several times by oral or parenteral administration (for example, injection, continuous infusion and administration to rectum locus).

EXAMPLE

The present invention will now be described in more detail with Test examples. However, the present invention is not limited to these examples.

The respective abbreviations have the following meaning.

FLCZ: fluconazole; MCFG: micafungin; AMPH-B: amphotericin B; 5-FC: flucytosine; VCZ: voriconazole The following compound was selected as the test compound. The chemical structural formula of this compound is illustrated below.

[Chemical Formula 3]

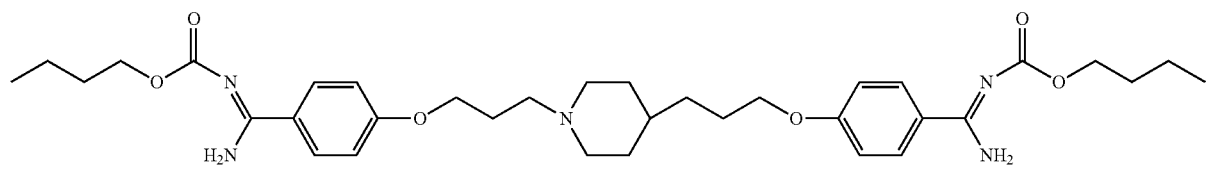

As the agents, fluconazole, micafungin, amphotericin B, voriconazole and flucytosine were selected.

Test Example 1

In Vivo Test (*Candida*)

In vivo activity was evaluated in murine systemic infection caused by *Candida albicans*.

Mice (4-week old (at infection) male ICR mice, 5 mice per group) were intraperitoneally administered 200 mg/kg of cyclophosphamide 4 days before infection and 100 mg/kg on the following day after infection. *Candida albicans* TIMM1623, which were prepared from overnight culture on a Sabouraud Dextrose Agar plate at 35° C., were suspended in sterile physiological saline solution. After counting cell number of the suspension with a biological microscope, the suspension was diluted with sterile physiological saline solution to give the inoculum solution. Systemic infection was induced in mice by intravenous inoculation of 0.2 mL of the inoculum solution into the tail vein ($2.6 \times 10^4$ CFU/mouse).

The test compound was dissolved in a small amount of 0.1 mol/L hydrochloric acid, and the solution was diluted with sterilized water to prepare predetermined concentrations.

Fluconazole (a commercial name: FLANOS intravenous drip solution 100 mg, made by Toyama Chemical Co., Ltd.) was diluted with sterilized water to prepare fluconazole solutions of predetermined concentrations.

Micafungin sodium (a commercial name: Funguard 50 mg for infusion, made by Astellas Pharma Inc.) was dissolved in sterile physiological saline solution to prepare micafungin solutions of predetermined concentrations.

Amphotericin B for injection (a commercial name: FUNGIZONE, made by Bristol pharmaceutical Ltd.) was dissolved in 5% glucose to prepare an amphotericin B solution of a predetermined concentration.

The test compound (0.25 and 0.5 mg/kg) and fluconazole (0.25 and 0.5 mg/kg) were orally administered. Micafungin (0.125 and 0.25 mg/kg) and amphotericin B (0.1 mg/kg) were subcutaneously administered. These administrations were conducted once 2 hours after the infection and then once daily for the following 6 days, totaling 7 times.

On one hand each of the agents was administered singly, on the other hand each of the agents was administered immediately after the test compound was administered.

The efficacy was evaluated on the basis of the survival rate on day 21 after infection.

The results of the combination therapy of the test compound and fluconazole against infection of *Candida albicans* are shown in Table 1, the results of the combination therapy of the test compound and micafungin are shown in Table 2 and the results of the combination therapy of the test compound and amphotericin B are shown in Table 3.

TABLE 1

| Administration composition | Test compound 0.5 mg/kg | FLCZ 0.25 mg/kg | FLCZ 0.5 mg/kg | Test compound 0.25 mg/kg FLCZ 0.25 mg/kg |
|---|---|---|---|---|
| Survival rate | 0 | 20 | 40 | 60 |

TABLE 2

| Administration composition | Test compound 0.5 mg/kg | MCFG 0.125 mg/kg | MCFG 0.25 mg/kg | Test compound 0.5 mg/kg MCFG 0.125 mg/kg |
|---|---|---|---|---|
| Survival rate | 0 | 0 | 40 | 80 |

TABLE 3

| Administration composition | Test compound 0.5 mg/kg | AMPH-B 0.1 mg/kg | Test compound 0.25 mg/kg AMPH-B 0.1 mg/kg |
|---|---|---|---|
| Survival rate | 0 | 20 | 80 |

In murine systemic infection caused by *Candida albicans*, the combined administration of the test compound and fluconazole, the test compound and micafungin, and the test compound and amphotericin B exhibited excellent therapeutic effects.

Test Example 2

In Vivo Test (*Aspergillus*)

In vivo activity was evaluated in murine systemic infection caused by *Aspergillus fumigatus*.

Mice (4-week old (at infection) male ICR mice, 5 mice per group) were intraperitoneally administered 200 mg/kg of cyclophosphamide 4 days before infection and 100 mg/kg on the following day after infection. Conidia suspension of *Aspergillus fumigatus* IFM46895 was diluted with sterile physiological saline solution containing 0.05% Tween 80 (manufactured by Difco Laboratories) in sterile physiological saline solution to give the inoculum solution. Systemic infection was induced in mice by intravenous inoculation of 0.2 mL of the inoculum solution into the tail vein ($1.6 \times 10^5$ CFU/mouse).

The test compound was dissolved in a small amount of 0.1 mol/L hydrochloric acid, and the solution was diluted with sterilized water to prepare predetermined concentrations.

Flucytosine (made by Sigma Company) was suspended in 0.5% methyl cellulose liquid to prepare predetermined concentrations for administration.

Voriconazole (a commercial name: Vfend 200 mg for intravenous use, made by Pfizer Inc.) was diluted with sterilized water to prepare voriconazole solutions of predetermined concentrations for administration.

The test compound (1 and 3 mg/kg), flucytosine (50 and 250 mg/kg) and voriconazole (5 and 10 mg/kg) were orally administered. The administrations were conducted once 2 hours after the infection and then once daily for the following 6 days, totaling 7 times.

On one hand each of the agents was administered singly, on the other hand each of the agents was administered immediately after the test compound was administered. The efficacy was evaluated on the basis of the survival rate on day 21 after infection.

The results of the combination therapy of the test compound and flucytosine against infection of *Aspergillus fumigatus* are shown in Table 4, and the results of the combination therapy of the test compound and voriconazole are shown in Table 5.

TABLE 4

| Administration composition | Test compound 3 mg/kg | 5-FC 250 mg/kg | Test compound 3 mg/kg 5-FC 50 mg/kg |
|---|---|---|---|
| Survival rate | 20 | 0 | 80 |

TABLE 5

| Administration composition | Test compound 1 mg/kg | Test compound 3 mg/kg | VCZ 10 mg/kg | Test compound 1 mg/kg VCZ 5 mg/kg |
|---|---|---|---|---|
| Survival rate | 0 | 20 | 0 | 40 |

In murine systemic infection caused by *Aspergillus fumigatus*, the combined administration of the test compound and flucytosine, the test compound and voriconazole exhibited excellent therapeutic effects. Especially, flucytosine, as usual, has almost no effect against *Aspergillus fumigatus*. In the above test, 250 mg/kg administration of flucytosine had no therapeutic effect. However, the combined administration of one fifth of 250 mg/kg of flucytosine and the test compound showed remarkably excellent antifungal effect.

Test Example 3

In Vivo Test (*Cryptococcus*)

In vivo activity was evaluated in murine systematic infection caused by *Cryptococcus neoformans*.

Mice (4-week old (at infection) male ICR mice, 5 mice per group) were intraperitoneally administered 200 mg/kg of cyclophosphamide 4 days before infection and 100 mg/kg on the following day after infection. *Cryptococcus neoformans* ATCC90112 cells, which were prepared from overnight culture on a Sabouraud Dextrose Agar plate at 35° C., were suspended in sterile physiological saline solution. After counting cell number of the suspension with a biological microscope, the suspension was diluted with sterile physiological saline solution to give the inoculum solution. Systematic infection was induced in mice by intravenous injection of 0.2 mL of the inoculum solution into the tail vein ($8.5 \times 10^4$ CFU/mouse).

The test compound was dissolved in a small amount of 0.1 mol/L hydrochloric acid, and the solution was diluted with sterilized water to prepare predetermined concentrations.

Fluconazole (a commercial name: FLANOS intravenous drip solution 100 mg, made by Toyama Chemical Co., Ltd.) was diluted with sterilized water to prepare fluconazole solutions of predetermined concentrations.

The test compound (0.5 and 1 mg/kg) and fluconazole (20 mg/kg) were orally administered. The administrations were conducted once 2 hours after the infection and then once daily for the following 6 days, totaling 7 times.

On one hand each of the agents was administered singly, on the other hand each of the agents was administered immediately after the test compound was administered. The efficacy was evaluated on the basis of the survival rate on day 21 after infection.

The results of the combination of the test compound and fluconazole against infection caused by *Cryptococcus neoformans* are shown in Table 6.

TABLE 6

| Administration composition | Test compound 1 mg/kg | FLCZ 20 mg/kg | Test compound 0.5 mg/kg FCZ 20 mg/kg |
|---|---|---|---|
| Survival rate | 0 | 20 | 60 |

In murine systematic infection caused by *Cryptococcus neoformans*, the combined administration of the test compound and fluconazole exhibited excellent therapeutic effects.

In addition, the test compound did not show toxicity at all when it was orally administered consecutively to mice, which were used the above tests, at 25 mg/kg for 2 weeks, and the test compound had high safety.

It is clear from the above results that the combination of the phenylamidine derivative or the salt thereof represented by general formula [1] with various antifungal agents or the like exhibits synergistic antifungal activity and treatment effects, and is effective in the treatment of fungal infections caused by fungal pathogens.

[Preparation]

Next, the present invention will now be described in more detail with Reference examples and Examples. However, the present invention is not limited to these examples.

The mixing ratio in the eluant is by capacity ratio and the carrier for the silica gel column chromatography is B.W. silica gel, BW-127ZH (Fujisilysia Chemical Ltd).

Reference Example 1

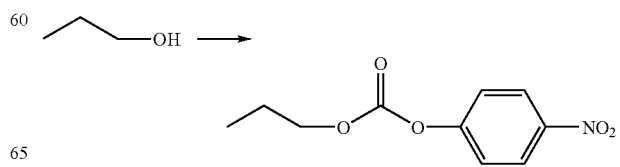

To tetrahydrofuran 10 mL solution of propanol 0.75 g and triethylamine 1.90 mL, a tetrahydrofuran 15 mL solution of 4-nitrophenyl chloroformate 2.50 g was dropped under ice-cooling. Ethyl acetate and water were added to the reaction mixture after stirring at room temperature for 20 minutes. After organic layer was separated, collected and washed with water and a saturated aqueous sodium chloride solution sequentially, the organic layer was dried over anhydrous magnesium sulfate, and followed by distilling off the solvent. After hexane was added to the residue, filtration of insolubles and removal of the solvent under reduced pressure yielded 4-nitrophenyl propylcarbonate 2.59 g as light yellow oil.

$^1$H-NMR (CDCl$_3$) δ value: 1.03 (3H, t, J=7.4Hz), 1.71-1.85 (2H, m), 4.26 (2H, t, J=6.7Hz), 7.39 (2H, d, J=9.0Hz), 8.28 (2H, d, J=9.0Hz)

Reference Example 2

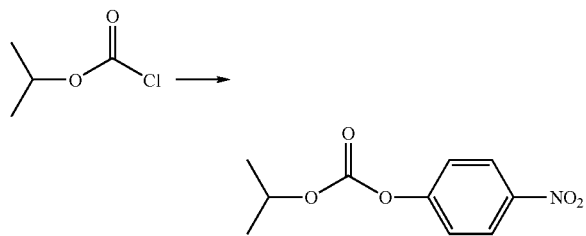

To tetrahydrofuran 30 mL solution of 4-nitrophenol 3.00 g and triethylamine 3.31 mL, isopropyl chloroformate 2.46 mL was dropped under ice-cooling. Ethyl acetate and water were added to the reaction mixture after stirring at the same temperature for 10 minutes. After organic layer was separated, collected and washed with a saturated aqueous sodium chloride solution, the organic layer was dried over anhydrous magnesium sulfate, followed by distilling off the solvent under reduced pressure. After the residue was dissolved in 50 ml of ethyl acetate and washed with 5% aqueous solution of potassium carbonate and a saturated aqueous sodium chloride solution sequentially, the organic layer was dried over anhydrous magnesium sulfate and followed by distilling off the solvent under reduced pressure to yield 4-nitrophenyl isopropylcarbonate 3.00 g as a light yellow solid.

$^1$H-NMR (CDCl$_3$) δ value: 1.41 (6H, d, J=6.3Hz), 4.96-5.07 (1H, m), 7.36-7.41 (2H, m), 8.25-8.30 (2H, m)

Reference Example 3

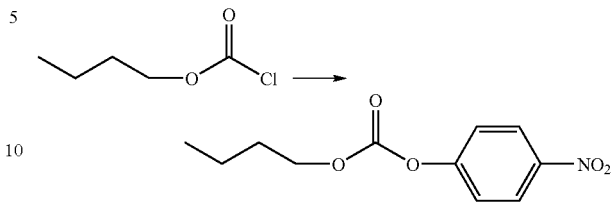

To tetrahydrofuran 30 mL solution of 4-nitrophenol 3.00 g and triethylamine 3.31 mL, butyl chloroformate 2.75 mL was dropped under ice-cooling. Ethyl acetate and water were added to the reaction mixture after stirring at the same temperature for 10 minutes. After organic layer was separated, collected and washed with a saturated aqueous sodium chloride solution, the organic layer was dried over anhydrous magnesium sulfate and followed by distilling off the solvent to yield 4-nitrophenyl butylcarbonate 4.60 g as light yellow oil.

$^1$H-NMR (CDCl$_3$) δ value: 0.99 (3H, t, J=7.4Hz), 1.41-1.52 (2H, m), 1.70-1.80 (2H, m), 4.30 (2H, t, J=6.6Hz), 7.36-7.41 (2H, m), 8.26-8.31 (2H, m)

Reference Example 4

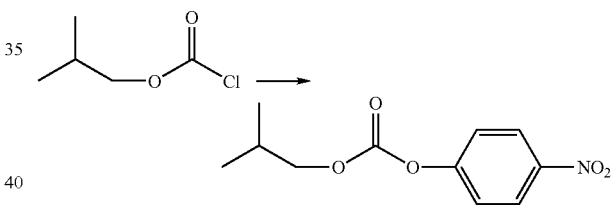

Similarly to the reference example 3, isobutyl 4-nitrophenyl carbonate 5.63 g was obtained as light yellow oil from 4-nitrophenol 3.00 g and isobutyl chloroformate 2.80 mL.

$^1$H-NMR (CDCl$_3$) δ value: 1.02 (6H, d, J=6.6Hz), 2.02-2.13 (1H, m), 4.08 (2H, d, J=6.6Hz), 7.39 (2H, d, J=9.1Hz), 8.28 (2H, d, J=9.1Hz)

Example 1

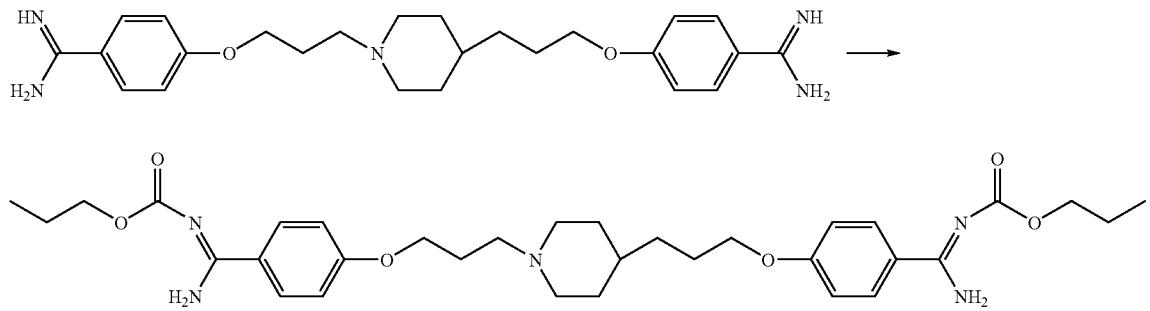

To N,N-dimethylformamide 15 mL solution of 4-nitrophenylpropyl carbonate 1.71 g, 4-{3-[4-(3-{4-[amino(imino)methyl]phenoxy}propyl)-1-piperidinyl]propoxy}benzamidine 1.50 g was added at room temperature, and the solution was stirred at the same temperature for 4 hours. Chloroform and water were added to the reaction mixture. After organic layer was separated, collected and washed with water, 5% aqueous solution of potassium carbonate twice and a saturated aqueous sodium chloride solution sequentially, the organic layer was dried over anhydrous magnesium sulfate, and followed by distilling off the solvent. The residue obtained was purified with silica gel column chromatography [eluant, chloroform:methanol=4:1]. The solid obtained was dissolved in chloroform, after the solution was washed with 5% aqueous solution of potassium carbonate and a saturated aqueous sodium chloride solution sequentially, the solution was dried over anhydrous magnesium sulfate, and followed by distilling off the solvent to provide 4-{3-[4-(3-{4-[amino(propoxycarbonylimino)methyl]phenoxy}propyl)-1-piperidinyl]propoxy}-N'-(propoxycarbonyl)benzamidine 1.25 g as a white solid.

$^1$H-NMR (CDCl$_3$) δ value: 0.99 (6H, t, J=7.4 Hz), 1.22-1.45 (5H, m), 1.66-1.86 (8H, m), 1.90-2.04 (4H, m), 2.46-2.54 (2H, m), 2.90-2.98 (2H, m), 3.99 (2H, t, J=6.5Hz), 4.06 (2H, t, J=6.3 Hz), 4.11 (4H, t, J=7.0 Hz), 6.88-6.96 (4H, m), 7.82-7.88 (4H, m)

Example 2

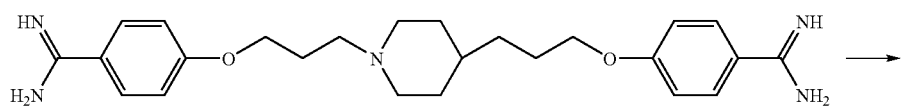

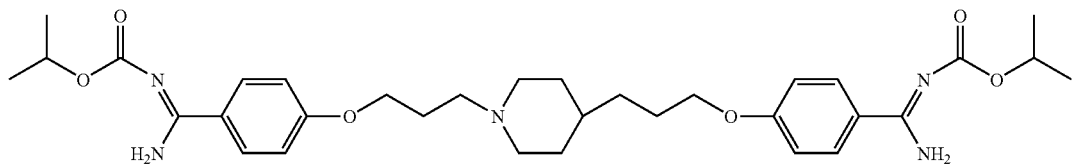

Similarly to the example 1, 4-{3-[4-(3-{4-[amino(isopropoxycarbonylimino)methyl]phenoxy}propyl)-1-piperidinyl]propoxy}-N'-(isopropoxycarbonyl)benzamidine 1.35 g of a white solid was obtained from 4-nitrophenyl isopropyl carbonate 1.71 g and 4-{3-[4-(3-{(4-[amino(imino)methyl]phenoxy}propyl)-1-piperidinyl]propoxy}benzamidine 1.50 g.

$^1$H-NMR (CDCl$_3$) δ value: 1.20-1.46 (5H, m), 1.34 (12H, d, J=6.3 Hz), 1.56-1.86 (4H, m), 1.88-2.04 (4H, m), 2.46-2.54 (2H, m), 2.90-2.98 (2H, m), 3.99 (2H, t, J=6.5Hz), 4.06 (2H, t, J=6.3Hz), 4.94-5.04 (2H, m), 6.88-6.96 (4H, m), 7.80-7.88 (4H, m)

Example 3

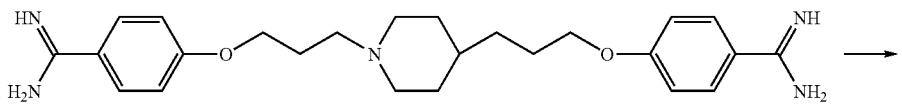

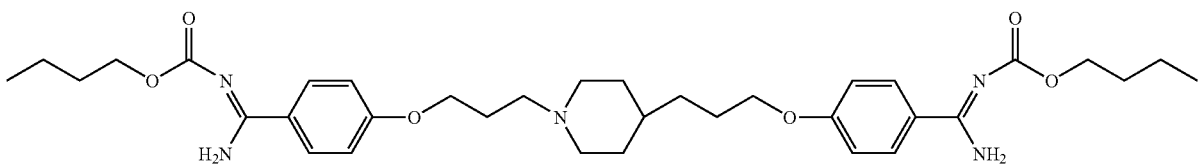

Similarly to the example 1, 4-{3-[4-(3-{4-[amino(butoxycarbonylimino)methyl]phenoxy}propyl)-1-piperidinyl]propoxy}-N'-(butoxycarbonyl)benzamidine 1.39 g of a white solid was obtained from butyl 4-nitrophenyl carbonate 1.82 g and 4-{3-[4-(3-{4-[amino(imino)methyl]phenoxy}propyl)-1-piperidinyl]propoxy}benzamidine 1.50 g.

$^1$H-NMR (CDCl$_3$) δ value: 0.95 (6H, t, J=7.3Hz), 1.20-1.50 (9H, m), 1.60-2.05 (12H, m), 2.45-2.54 (2H, m), 2.90-3.00 (2H, m), 3.99 (2H, t, J=6.6Hz), 4.06 (2H, t, J=6.3 Hz), 4.16 (4H, t, J=6.8Hz), 6.88-6.96 (4H, m), 7.82-7.88 (4H, m)

Example 4

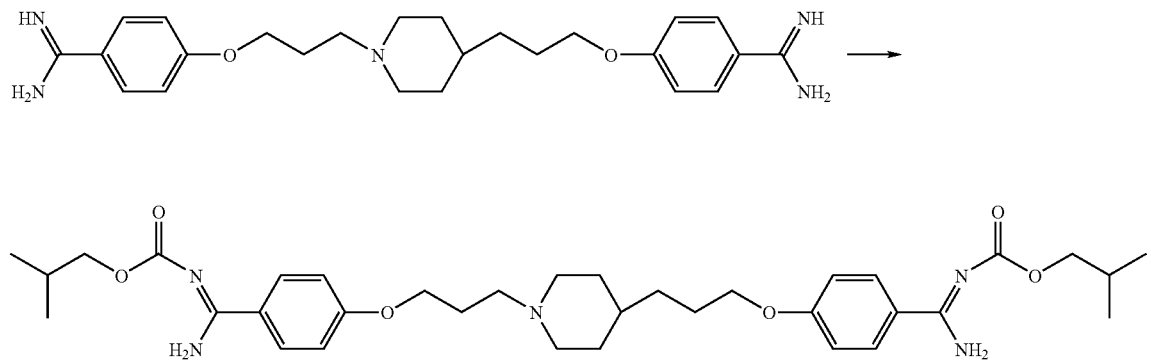

To N,N-dimethylformamide 15 mL solution of isobutyl 4-nitrophenyl carbonate 1.82 g, 4-{3-[4-(3-{4-[amino(imino)methyl]phenoxy}propyl)-1-piperidinyl]propoxy}benzamidine 1.50 g was added at room temperature, and the solution was reacted at the same temperature for 17 hours. Chloroform and water were added to the reaction mixture. After organic layer was separated, collected and washed with water, 5% aqueous solution of potassium carbonate and a saturated aqueous sodium chloride solution sequentially, the organic layer was dried over anhydrous magnesium sulfate, and followed by distilling off the solvent. The residue obtained was purified with silica gel column chromatography [eluant, chloroform:methanol=4:1]. The residue obtained was dissolved in chloroform, after the solution was washed with 5% aqueous solution of potassium carbonate and a saturated aqueous sodium chloride solution sequentially, the solution was dried over anhydrous magnesium sulfate, and followed by distilling off the solvent to provide 4-{3-[4-(3-{4-[amino(isobutoxycarbonylimino)methyl]phenoxy}propyl)-1-piperidinyl]propoxy}-N'-(isobutoxycarbonyl)benzamidine 1.43 g as a white solid.

$^1$H-NMR (CDCl$_3$) δ value: 0.99 (12H, d, J=6.8Hz), 1.20-1.45 (5H, m), 1.55-2.12 (10H, m), 2.46-2.53 (2H, m), 2.90-3.00 (2H, m), 3.94 (4H, d, J=6.8Hz), 3.99 (2H, t, J=6.5Hz), 4.06 (2H, t, J=6.3Hz), 6.88-6.96 (4H, m), 7.80-7.90 (4H, m).

Pharmaceutical Example 1

The compound 100 mg obtained in the example 3 and sodium chloride 18 g were added to water for injection 1.8 L. It was adjusted to pH 4 with hydrochloric acid and dissolved, and diluted to 2 L of total volume with water for injection. The dissolved solution was filtered through a membrane filter of 0.22 μm, and the obtained pharmaceutical solution 100 mL was packed and sealed into an ampule to give injections.

Pharmaceutical Example 2

The compound 500 mg obtained in the example 3, lactose 350 mg, corn starch 250 mg and crystalline cellulose [a commercial name: CEOLUS PH101: Asahi Kasei Chemicals Corporation] 400 mg were mixed, 5% hydroxypropylcellulose aqueous solution 0.6 mL and water were added to the mixture and the mixture was kneaded. After the mixture obtained was dried at 60° C., cross povidone [a commercial name: Kollidon CL, BASF] 100 mg, light anhydrous silicic acid 100 mg and magnesium stearate 20 mg were added to the mixture and the mixture was mixed. The mixture 175 mg was formulated into circular tablets having a diameter of 8 mm to give tablets.

Pharmaceutical Example 3

The compound 500 mg obtained in the example 3, lactose 200 mg and corn starch 530 mg were mixed, 5% hydroxypropylcellulose aqueous solution 0.6 mL and water were added to the mixture and the mixture was kneaded. After the mixture obtained was dried at 60° C., cross povidone [a commercial name: Kollidon CL, BASF] 70 mg, crystalline cellulose [a commercial name: CEOLUS PH302, Asahi Kasei Chemicals Corporation] 180 mg and magnesium stearate 20 mg were added to the mixture, and the resulting mixture was mixed. The mixture 150 mg was packed into 3-type gelatin capsule to give capsules.

[Industrial Applicability]

The pharmaceutical composition comprising the new phenylamidine derivative or a salt thereof, and one or more antifungal agents selected from azole antifungal agents, polyene antifungal agents, candin antifungal agents and fluoropyrimidine antifungal agents, has strong antifungal activity and is useful for treating fungal infections. The method for combination use of these antifungal agents is useful as an excellent treatment method of fungal infections.

The invention claimed is:
1. A pharmaceutical composition for treating fungal infections, comprising a phenylamidine derivative or a salt thereof, represented by a general formula,

[CHEMICAL FORMULA 1]

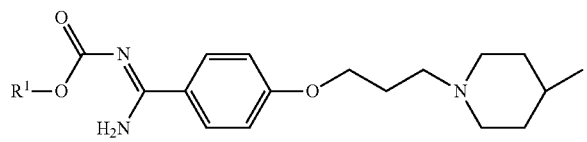

[CHEMICAL FORMULA 2]

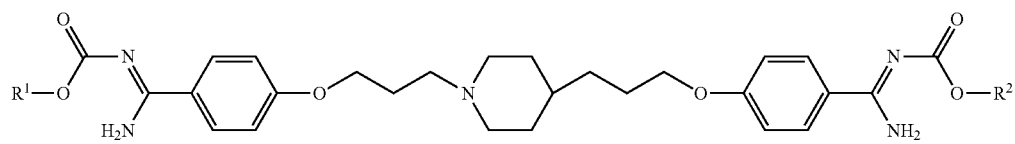

-continued

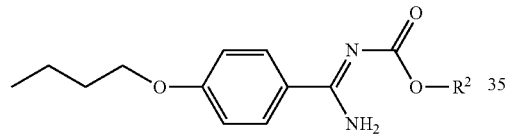

wherein both $R^1$ and $R^2$ represent a $C_{3-4}$alkyl group; and at least one agent selected from an azole antifungal agent, a polyene antifungal agent, a candin antifungal agent and a fluoropyrimidine antifungal agent.

2. The pharmaceutical composition according to claim 1, wherein the at least one agent is an azole antifungal agent.

3. The pharmaceutical composition according to claim 1, wherein the at least one agent is a polyene antifungal agent.

4. The pharmaceutical composition according to claim 1, wherein the at least one agent is a candin antifungal agent.

5. The pharmaceutical composition according to claim 1, wherein the at least one agent is a fluoropyrimidine antifungal agent.

6. The pharmaceutical composition according to claim 2, wherein the azole antifungal agent is a triazole antifungal agent.

7. The pharmaceutical composition according to claim 6, wherein the triazole antifungal agent is selected from the group consisting of fluconazole, fosfluconazole, voriconazole and itraconazole.

8. The pharmaceutical composition according to claim 3, wherein the polyene antifungal agent is amphotericin B or a liposomal formulation thereof.

9. The pharmaceutical composition according to claim 4, wherein the candin antifungal agent is micafungin.

10. The pharmaceutical composition according to claim 1, wherein the fungal infection is caused by a fungal pathogen selected from *Candida, Cryptococcus* and *Aspergillus*.

11. A method of treating a fungal infection caused by fungal pathogens, comprising administering to a subject in need therof, a phenylamidine derivative or a salt thereof, represented by a general formula, wherein both $R^1$ and $R^2$ represent a $C_{3-4alkyl}$ group; and at least one agent selected from an azole antifungal agent, a polyene antifungal agent, a candin antifungal agent and a fluoropyrimidine antifungal agent.

12. The method according to claim 11, wherein the at least one agent is an azole antifungal agent.

13. The method according to claim 11, wherein the at least one agent is a polyene antifungal agent.

14. The method according to claim 11, wherein the at least one agent is a candin antifungal agent.

15. The method according to claim 11, wherein the at least one agent is a fluoropyrimidine antifungal agent.

16. The method according to claim 12, wherein the azole antifungal agent is a triazole antifungal agent.

17. The method according to claim 16, wherein the triazole antifungal agent is selected from the group consisting of fluconazole, fosfluconazole, voriconazole and itraconazole.

18. The method according to claim 13, wherein the polyene antifungal agent is amphotericin B or liposomal formulations thereof.

19. The method according to claim 14, wherein the candin antifungal agent is micafungin.

20. The method according to claim 11, wherein the fungal infection is caused by a fungal pathogen selected from *Candida, Cryptococcus* and *Aspergillus*.

* * * * *